US00PP26152P2

(12) United States Plant Patent
Williams

(10) Patent No.: US PP26,152 P2
(45) Date of Patent: Nov. 24, 2015

(54) *COLOCASIA* PLANT NAMED 'IMPERIAL GIGANTE'

(50) Latin Name: ***Colocasia* hybrid**
Varietal Denomination: Imperial Gigante

(71) Applicant: Brian Paul Williams, Louisville, KY (US)

(72) Inventor: Brian Paul Williams, Louisville, KY (US)

(73) Assignee: BRIAN'S BOTANICALS, Louisville, KY (US)

( * ) Notice: Subject to any disclaimer, the term of this patent is extended or adjusted under 35 U.S.C. 154(b) by 102 days.

(21) Appl. No.: 13/987,210

(22) Filed: Jul. 11, 2013

(51) Int. Cl.
*A01H 5/00* (2006.01)

(52) U.S. Cl.
USPC ..... Plt./373

(58) Field of Classification Search
USPC ..... Plt./373
CPC ..... A01H 5/00; A01H 5/12
See application file for complete search history.

(56) References Cited

PUBLICATIONS

Plants Nouveau retrieved from internet Dec. 3, 2014.*

* cited by examiner

*Primary Examiner* — Keith Robinson
(74) *Attorney, Agent, or Firm* — Penny J. Aguirre

(57) ABSTRACT

A new cultivar of *Colocasia* plant named 'Imperial Gigante', that is characterized by its large leaves that are light green and suffused with black between bright yellow-green veins, its leaves that are held horizontal to the petioles, its large tubers when mature, and its small tuberous rhizomes that are produced at the base of mature plants.

2 Drawing Sheets

Botanical classification: *Colocasia* hybrid.
Cultivar designation: 'Imperial Gigante'.

BACKGROUND OF THE INVENTION

The present invention, *Colocasia* 'Imperial Gigante', relates to a new and distinct interspecific hybrid of *Colocasia*, hereinafter referred to by its cultivar name, 'Imperial Gigante'. 'Imperial Gigante' is a new tropical plant used as a landscape and container plant in tropical and subtropical areas.

The new cultivar was derived from a controlled breeding program conducted by the Inventor at his nursery in Louisville, Ky. The overall purpose of the breeding program is to make selections of *Colocasia* plants that are unique with large leaves and vigorous growth habits. 'Imperial Gigante' arose from a cross made in June of 2010 between an unnamed plant of a *Colocasia* of hybrid origin from the Inventor's breeding program as the female parent and an unnamed plant of *Colocasia gigantea* as the male parent. 'Imperial Gigante' was selected as a single unique plant in June of 2012 from amongst the seedlings derived from the above cross.

Asexual propagation of the new cultivar was first accomplished by in vitro propagation under the direction of the Inventor in Eustis, Fla. in July of 2012. Asexual propagation by in vitro propagation has shown that the characteristics of the new cultivar are stable and reproduced true to type in successive generations.

SUMMARY OF THE INVENTION

The following traits have been repeatedly observed and represent the characteristics of the new cultivar. These attributes in combination distinguish 'Imperial Gigante' as a new and unique cultivar of *Colocasia*.

1. 'Imperial Gigante' exhibits large leaves.
2. 'Imperial Gigante' exhibits leaves that are light green and suffused with black between bright yellow-green veins.
3. 'Imperial Gigante' exhibits leaves that are held horizontal to the petioles.
4. 'Imperial Gigante' exhibits large tubers when mature.
5. 'Imperial Gigante' exhibits small tuberous rhizomes at the base of mature plants.

The female parent of 'Imperial Gigante', an unnamed plant of *Colocasia* of hybrid origin, differs from 'Imperial Gigante' in having smaller leaves that are held vertically and solid black in color with black veins. The male parent of 'Imperial Gigante', an unnamed plant of *Colocasia gigantea*, differs from 'Imperial Gigante' in having leaves that are green with green veins and in lacking tuberous rhizomes. 'Imperial Gigante' can be most closely compared to the *Colocasia esculenta* cultivars 'Black Magic' (not patented) and 'Mojito' (U.S. Plant Pat. No. 21,995). Both are similar to 'Imperial Gigante' in having large leaves that have dark coloration. 'Black Magic' differs from 'Imperial Gigante' in being shorter in height, in having leaves that are solid black in color and rarely producing tubers. 'Mojito' differs from 'Imperial Gigante' in being shorter in height and in having leaves that are variegated (green with black mottling), in lacking yellow-green veins, and in rarely producing tubers.

BRIEF DESCRIPTION OF THE DRAWINGS

The accompanying colored photographs illustrate the overall appearance and distinct characteristics of the new *Colocasia*, 'Imperial Gigante'. The photographs were taken of plants about 2 years in age as grown outdoors under 6 mm poly and natural lighting in Louisville, Ky. and planted in a trial garden.

Figure 1:
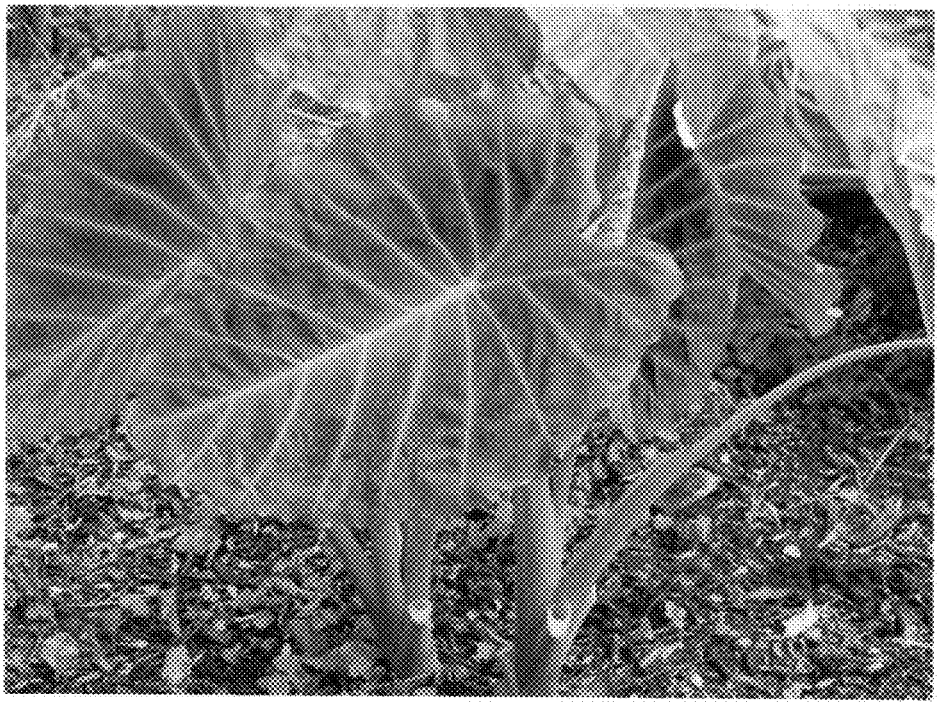
FIG. 1 provides an overall view of the mature foliage and plant habit of 'Imperial Gigante' in spring.
Figure 2:
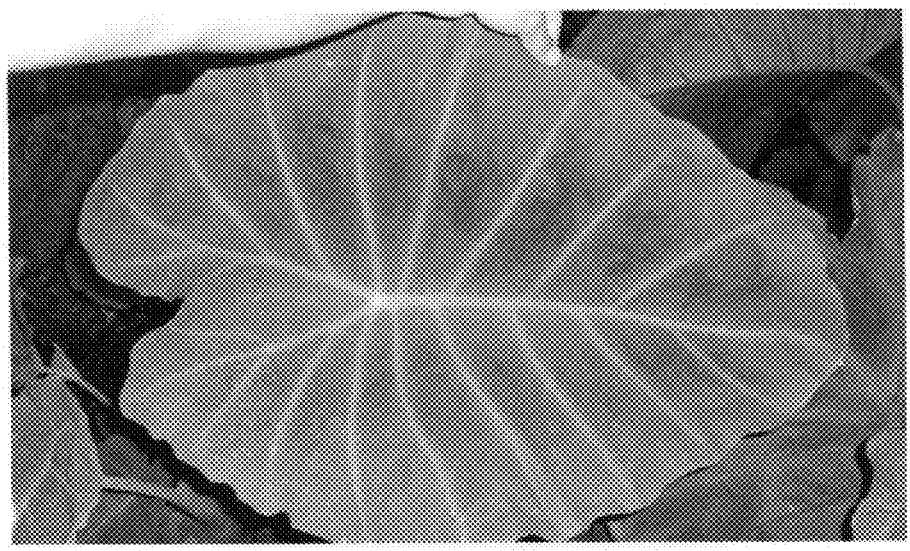

The photograph in FIG. 2 provides a close-up view of a spring leaf of 'Imperial Gigante'.

Figure 3:
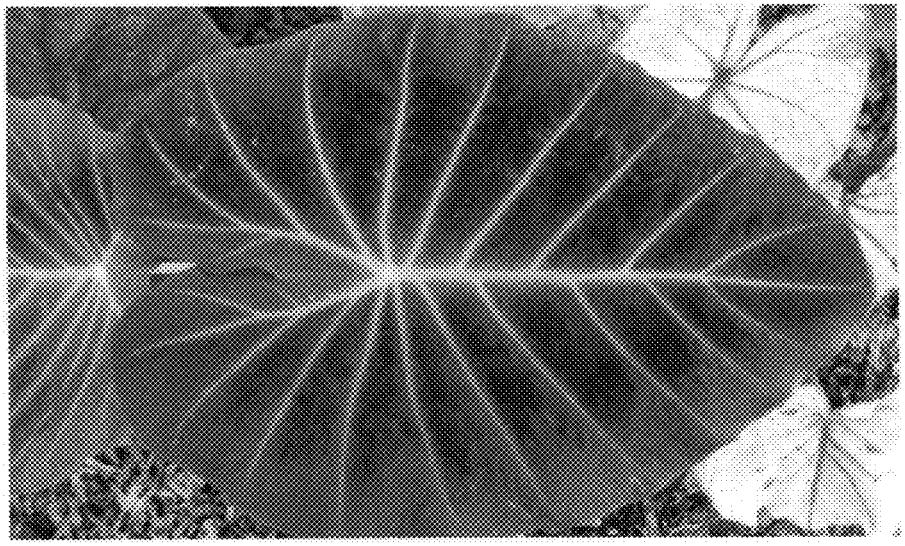

The photograph in FIG. 3 provides a close-up view of a summer leaf of 'Imperial Gigante'.

The colors in the photographs are as close as possible with the photographic and printing technology utilized and the color values cited in the Detailed Botanical Description accurately describe the colors of the new *Colocasia*.

DETAILED BOTANICAL DESCRIPTION OF THE PLANT

The following is a detailed description of three year-old plants of the new cultivar as grown outdoors in full sun under 2 mm poly greenhouse plastic in Louisville, Ky. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type.*—Tropical perennial.

*Plant habit.*—Upright, stemless.

*Height and spread.*—Reaches 1.8 to 2.1 m (6 to 7 ft) in height and 1.2 to 2.1 m (4 to 7 ft) in width.

*Cold hardiness.*—At least to U.S.D.A. Zone 7.

*Diseases and pests.*—No particular resistance or susceptibility has been shown to diseases and pests.

*Roots.*—Fleshy, produced in a compact mass, NN155B in color.

*Root development.*—Tissue culture plugs will fully root in a one-gallon container in 2 to 3 months with sufficient heat and sun.

*Corm.*—Rounded, an average of 6.9 cm in diameter, NN155B in color.

*Propagation type.*—In vitro propagation is preferred.

*Growth rate.*—Vigorous.

*Stem description.*—Stemless, can produce tubers an average of 6.9 cm in diameter at base after one year of growth.

*Rhizomes.*—Form around base of plant, emerge from with scales 178A in color, about 2 cm in diameter when they emerge before they elongate.

Foliage description:

*Leaf shape.*—Ovate-slightly oblong.

*Leaf division.*—Single.

*Leaf base.*—Cordate.

*Leaf apex.*—Acute, slightly cuspidate.

*Leaf venation.*—Pinnate, color in spring; upper surface 144A, lower surface 145C, color in summer upper surface 149C, lower surface 145B.

*Leaf margins.*—Undulate.

*Leaf attachment.*—Petiolate.

*Leaf arrangement.*—Alternate.

*Leaf surface.*—Upper surface and lower surface; glabrous, almost velvety.

*Leaf orientation.*—Held horizontal.

*Leaf color.*—Spring foliage upper surface; 147A, blending into 143B towards margins, with a flush of 202A between veins, spring foliage lower surface; 137C and lightly suffused between the veins with N187A, summer foliage upper surface; 147A and suffused with 202A between veins, summer foliage lower surface; 147B and slightly suffused with 202A.

*Leaf size.*—Up to 91.44 cm in length and 61 cm in width.

*Leaf sinus.*—An average of 14 cm in depth on a mature leaf.

*Petioles.*—Held erect to semi-erect, about 1.83 m in length and 2.54 cm in distal diameter and 10.16 cm in proximal diameter, glaucous surface, 145B in color with fine and sparse dots of 144B on upper portion and fine and sparse dots of 166A near the base, basal sheath portion is narrowly triangular in shape, an average of 10 cm in diameter and 18 cm in length, both surfaces; 145B in color, glabrous and satiny.

Inflorescence description:

*Blooming period.*—Two to three weeks in mid to late summer in Louisville, Ky.

*Inflorescence type.*—Spadix surrounded by a spathe, male portion held above female portion, only female flowers were developed.

*Inflorescence size.*—Average of 26 cm in length and 7 cm in width.

*Inflorescence bud.*—Linear to slightly narrow oblanceolate in shape, glabrous and smooth surface, an average of 16 cm in length, male portion; 1.9 cm in width, female portion; 2.8 cm in width, male portion; 150D in color and female portion; 144C.

*Flower fragrance.*—None.

*Lastingness of inflorescence.*—Inflorescence blooms intermittently during the bloom period, individual flowers last about 2 to 3 weeks.

*Inflorescence/flower quantity.*—Intermittent throughout the bloom season, sets of 3 or more, an average of 270 female flowers per spadix, male flowers were undeveloped.

*Spathe.*—Hooded, bract, subtending spadix, elliptic in shape, entire margin, acute apex, 19.5 cm in length and 7 cm in width, inner surface; coriaceous and smooth, outer surface; coriaceous and textured with linear grooves, lasts 5 to 7 days, color: when opening and fully open on inner and outer rear surface; 150D.

*Spadix.*—Male portion above female zone, upright cylindrical shape (phallus-like), apex narrowly pointed, about 9 mm in diameter (not including ovary) and 12.3 cm in length, male zone; 9 mm in diameter and 8.4 cm in length, color immature and mature 149C to 149D, female zone; 1.7 cm in diameter and 3.1 length, color immature and mature 144C to 144D with 149D at the tips.

*Peduncle.*—Triangular in shape, grows from base of plant, up to 30.5 cm in length and 5.7 cm in diameter, held at 20° angle, durable and strong, 144A to 144A in color, glabrous surface.

Reproductive organs:

*Gynoecium.*—1 pistil, 5 stigmas are 149D in color, ovary is flattened obovate in shape and 144C to 144D in color.

*Androcoecium.*—Undeveloped.

*Fruit and seed.*—Sterile.

It is claimed:

1. A new and distinct cultivar of *Colocasia* plant named 'Imperial Gigante' as herein illustrated and described.

* * * * *